(12) United States Patent
Esten

(10) Patent No.: US 8,746,517 B2
(45) Date of Patent: Jun. 10, 2014

(54) GLOVE ARRANGEMENT

(76) Inventor: Noel K. Esten, El Segundo, CA (US)

( * ) Notice: Subject to any disclaimer, the term of this patent is extended or adjusted under 35 U.S.C. 154(b) by 128 days.

(21) Appl. No.: 13/317,575

(22) Filed: Oct. 20, 2011

(65) Prior Publication Data

US 2013/0098953 A1    Apr. 25, 2013

(51) Int. Cl.
*A47G 25/90*    (2006.01)
*A41D 19/00*    (2006.01)
*A47G 25/00*    (2006.01)

(52) U.S. Cl.
USPC .............................................. 223/111; 2/160

(58) Field of Classification Search
USPC .................. 223/111, 112; 2/159–170; 24/3.1; 224/933
See application file for complete search history.

(56) References Cited

U.S. PATENT DOCUMENTS

| | | | | |
|---|---|---|---|---|
| 3,428,962 | A * | 2/1969 | Slimovitz | 2/48 |
| 5,864,925 | A * | 2/1999 | McGee | 24/3.11 |
| 6,427,883 | B1* | 8/2002 | Esten | 223/111 |
| 2004/0245268 | A1* | 12/2004 | Grinberg | 221/34 |
| 2007/0075106 | A1* | 4/2007 | Meeh | 224/274 |
| 2010/0192277 | A1* | 8/2010 | Powell | 2/160 |
| 2011/0204105 | A1* | 8/2011 | Kelly et al. | 223/111 |
| 2012/0227153 | A1* | 9/2012 | Laycock et al. | 2/88 |
| 2013/0042387 | A1* | 2/2013 | Kwon | 2/161.2 |

* cited by examiner

*Primary Examiner* — Ismael Izaguirre
(74) *Attorney, Agent, or Firm* — Raymond Y. Chan; David and Raymond Patent Firm

(57) ABSTRACT

A glove arrangement includes at least a glove and a retaining arrangement, wherein the retaining arrangement detachably retain the glove on an environment surface so that the glove is adapted to move between an in-use position and a storing position, wherein when the glove is at the in-use position, the glove is departed from the environment surface for operation by a user, wherein at the storing position, the glove is retained on the environment surface.

5 Claims, 11 Drawing Sheets

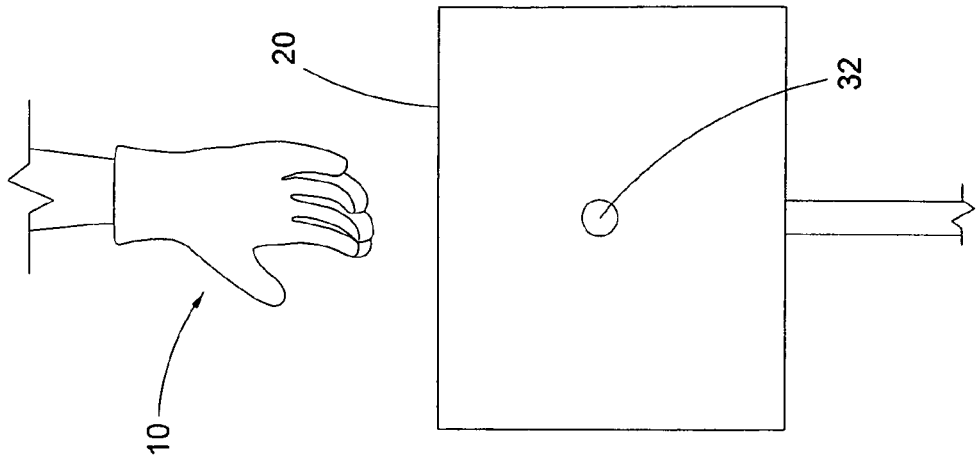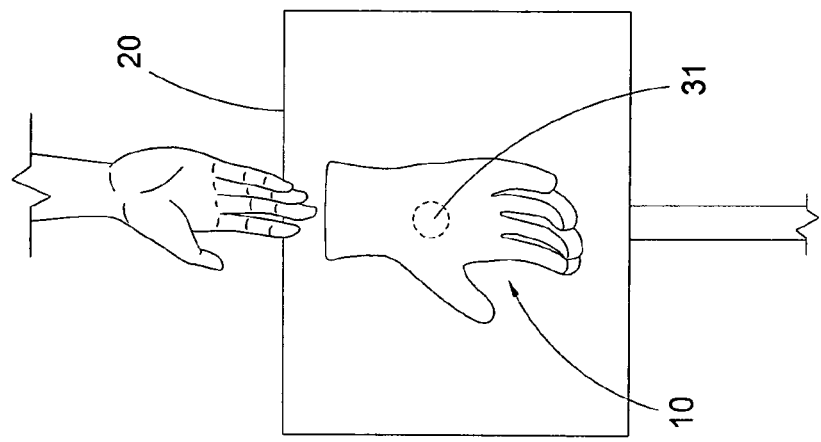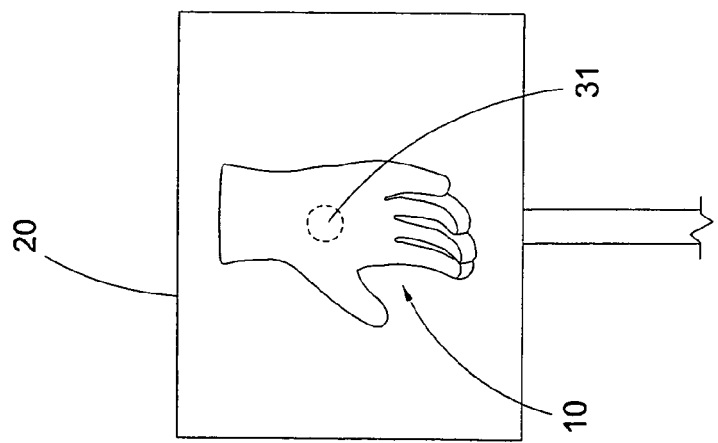

GLOVE ARRANGEMENT

BACKGROUND OF THE PRESENT INVENTION

1. Field of Invention

The present invention relates to gloves, and more particularly to a glove arrangement enabling a user easily wearing a glove body in a donning and doffing manner without touching the outer surface of the glove body by a hand of the user.

2. Description of Related Arts

Gloves, such as disposable plastic gloves, latex gloves and wool mitts, are used for protecting our hands or keeping our hands warm. The gloves are widely used in food processing, medical treatment and health, industrial security, household sanitation and so on. For example, the work staff are required to clean and disinfect their hands and then wear sterilized gloves before getting into a food manufacturing work shop, so that the sanitation of the food is ensured; A medical care personnel such as a doctor and a nurse has to wear gloves during a medical treatment process for preventing the infection of bacteria and virus; In chemical industries and biological research, people also wear gloves for preventing poisonous and toxic chemical substance from contacting with their hands; And in our daily lives, the gloves are used for sanitation housework, or people may wear them for preventing burning themselves when they are using a microwave oven or a toaster.

It should be noticed that although when people wear on gloves they can keep their hands from contacting with bacteria, virus, poisonous and toxic chemical substance, they may still have chance to skin contact with them while they remove the gloves from their hands and wear the used gloves back to their hands, because a hand of user only succeed in wearing a glove body with the help of the other hand of the user. For example, when the user is wearing a glove to his left hand, he may user his right hand to hold the glove so that his hand can easily don the glove, in addition, the right hand may be further employed for optimizing the glove body to a desire position; likewise, when the user wants to remove the glove from his right hand, he may also have to turn to his right hand for help. It is thus can be seen that when the user wears on a glove to his left hand in a donning and doffing manner, his right hand will inevitably have contact with the glove body. And thus the right hand of the user may have to skin contact with bacteria, virus, poisonous and toxic chemical substance on the outer surface of the glove body. In other words, a conventional glove cannot enable the user to wear the glove body in a donning and doffing manner without touching the outer surface of the glove body by a hand of the user, which brings inconvenience to the user. And even further, when toxic or carcinogenic substance is used in a chemical process or an experiment, we must make sure that the hands of the user do not contact with the glove body for health purpose; and during a food manufacturing process, the food has contact with the outer surface of the glove body, in order to guarantee the hygiene of the food, the hands of the user are prohibited to have contact with the glove body in order to avoid contamination of the gloves. Therefore, it is hard for the conventional gloves to meet the requirement.

On the other hand, conventional gloves also occupy a lot of space and room, in other words, the user has to employ storing tools like hanging hook or storing case to provide a storing position for the gloves. For example, a storing cabinet may be introduced for storing gloves at the gate of a work shop or a lab; a special space should be spared for a household mitt. And when a user wants to use the gloves, he has to find the storing position of the gloves first, it is especially inconvenient for a stranger, visitor to a new environment or someone who has not got familiar with his work environment. And when an emergency takes places, it will be a waste of time if he cannot immediately find the gloves. In addition, when he finds the gloves, he still has to take down the gloves from the hanging hook or takes out the gloves from the storing cabinet and then wears them with cooperation of both hands. Therefore, a glove arrangement adapted for easy storing and convenient donning and doffing is required.

SUMMARY OF THE PRESENT INVENTION

The main object of the present invention is to provide a glove arrangement which is easy for storing and enables a user wearing a glove body in a donning and doffing manner without touching the outer surface of the glove body by a hand of the user.

Another object of the present invention is to provide a glove arrangement comprising at least a glove and a retaining arrangement, wherein the retaining arrangement detachably retains the glove on an environment surface so that the glove is adapted to move between an in-use position and a storing position, wherein when the glove is at the in-use position, the glove is departed from the environment surface for operation by a user, wherein at the storing position, the glove is retained on the environment surface, and thus with the aiding of the retaining arrangement, the glove of the glove arrangement is easy for storing and using.

Another object of the present invention is to provide a glove arrangement comprising at least a glove and a retaining arrangement, enabling a user directly putting his hand into or retract his hand out of a receiving cavity of the glove so as to wear the glove in a donning or a doffing manner, therefore, the hands of the user do not have skin contact with the outer surface of the glove during the donning and doffing process.

Another object of the present invention is to provide a glove arrangement comprising at least a glove and a retaining arrangement, wherein when the retaining arrangement detachably couples the glove to an environment surface, simply by putting into or retract out from the receiving cavity of the glove, the user is able to don and doff a glove with one hand without the help of the other hand.

Another object of the present invention is to provide a glove arrangement comprising two glove bodies, the two glove bodies are detachably coupled with the environment surface by the retaining arrangement so that the two hands of the user is able to simultaneously don and doff the two glove bodies respectively.

Additional advantages and features of the invention will become apparent from the description which follows, and may be realized by means of the instrumentalities and combinations particular point out in the appended claims.

According to the present invention, the foregoing and other objects and advantages are attained by a glove arrangement comprising at least a glove and a retaining arrangement, wherein the retaining arrangement detachably retain the glove on an environment surface so that the glove is adapted to move between an in-use position and a storing position, wherein when the glove is at the in-use position, the glove is departed from the environment surface for operation by a user, wherein at the storing position, the glove is retained on the environment surface.

In accordance with another aspect of the invention, the glove arrangement of the present invention further comprises an auxiliary element, wherein the environment surface is a surface of the auxiliary element, wherein the retaining arrangement comprises a first retaining member provided on the glove and a second retaining member provided on the auxiliary element, wherein the first retaining member is detachably coupled with the second retaining member in such a manner that the glove is capable of being detachably mounted to the auxiliary element.

Still further objects and advantages will become apparent from a consideration of the ensuing description and drawings.

These and other objectives, features, and advantages of the present invention will become apparent from the following detailed description, the accompanying drawings, and the appended claims.

BRIEF DESCRIPTION OF THE DRAWINGS

FIG. 3A to FIG. 3E are schematic views illustrating the wearing of the glove in a donning and doffing manner according to the above preferred embodiment of the present invention.

DETAILED DESCRIPTION OF THE PREFERRED EMBODIMENT

Referring to FIG. 1, FIG. 2, FIG. 3A, FIG. 3B, FIG. 3C, FIG. 3D and FIG. 3E of the drawings, a glove arrangement according to a preferred embodiment of the present invention is illustrated, wherein the glove arrangement comprises at least a glove 10, an auxiliary element 20 and a retaining arrangement 30. Wherein the glove 10 is debatably coupled with the auxiliary element 20 by the retaining arrangement 30 in such a manner that the glove is adapted to move between an in-use position and a storing position, wherein when the glove 10 is at the in-use position, the glove 10 is departed from the auxiliary element 20 for operation by a user, and at the storing position, the glove 10 is retained on the auxiliary element 20. In other words, when the user wears the glove 10 in a donning manner, the glove 10 moves from the storing position to the in-use position, and when the user wears the glove 10 in a doffing manner, the gloves moves from the in-use position to the storing position.

Figure 1:
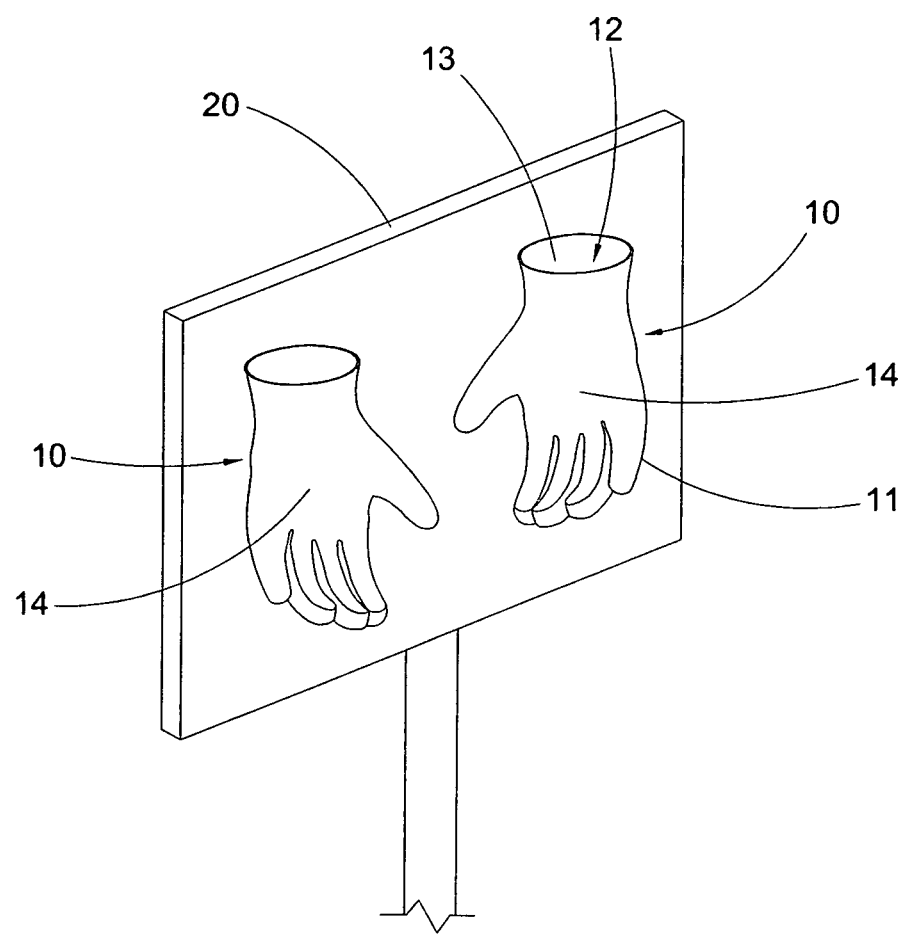
FIG. 1 is a perspective view of a glove arrangement according to a preferred embodiment of the present invention.
Figure 2:
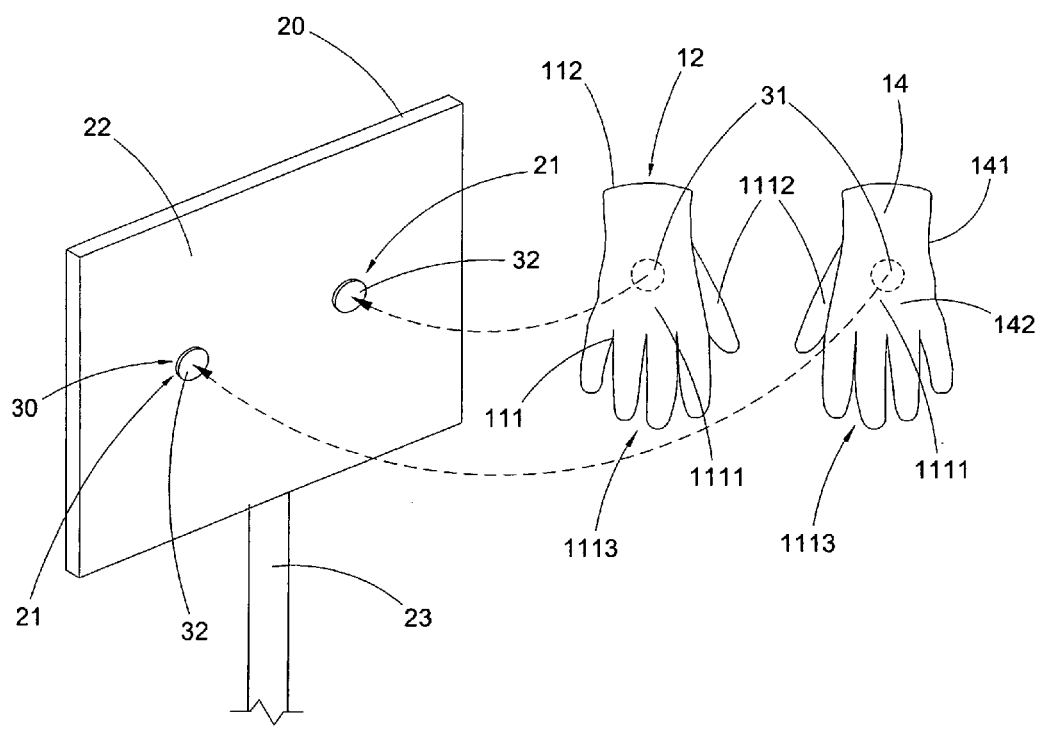
FIG. 2 is an exploded view of the glove arrangement according to the above preferred embodiment of the present invention.

According to different application environment, the glove 10 can be any kinds of gloves such as latex glove and wool mitt. Referring to FIG. 2 of the drawing, a typical glove 10 comprises a glove body 11, wherein the glove body 11 defining a receiving cavity 12 and an opening 13 communicating with the receiving cavity 12 in such a manner that the receiving cavity 12 is communicated outside of the glove body 11, and thus a user can put his hand into the receiving cavity 12 through the opening 13. Therefore, the hand of the user is secured in the receiving cavity 12 so that the glove 10 can protect the hand or keep warm of the hand. For example, when the glove 10 is introduced into the chemical industry, the glove 10 is made of chemical resistant material so that the hand of the user will not have skin contact with toxic or even carcinogenic substance; when the glove 10 is employed into the food manufacturing process or biological experiments, the glove 10 can prevent the hand from contacting with bacteria or virus; in our daily life, such as when we are using a microwave oven or a toaster, the glove 10 may be brought into for keep us from burning our hands.

The auxiliary element 20 provides a retention spot 21, wherein the glove body 11 is detachably coupled on the retention spot 21 in such a manner that the glove 10 is detachably coupled with the auxiliary element 20. More specifically, the glove 10 is detachably coupled with the auxiliary element 20 via the retaining arrangement 30. Accordingly, the retaining arrangement 30 comprises a first retaining member 31 and a second retaining member 32, wherein the first retaining member 31 is provided on the glove body 11 of the glove 10, wherein the second retaining member 32 is provided on the retention spot 21 of the auxiliary element 20, and the first retaining member 31 is detachably coupled with the second retaining member 32 in such a manner that the glove body 11 is detachably mounted on the retention spot 21 so that the glove 10 is adapted for moving between the in-use position and the storing position.

The first retaining member 31 and the second retaining member 32 are corresponding magnetic members, Velcro (loop and hook type fastener) members or bonding members, so that the first retaining member 31 is capable of detachably coupling with the second retaining member 32, it is worth mentioning that the engaging force between the first retaining member 31 and the second retaining member 32 is strong enough so that the glove 10 will not slip off or fall off from the retention spot 21 when the user wear on the glove 10.

Preferably, the first retaining member 31 is magnetically coupled with the second retaining member 32, because the magnetic members are more durable in comparison with the Velcro members and the bonding members. For example, when the glove 10 is used in chemical industry, the chemical substance may destroy the Velcro members and the bonding members, but a magnetic member may have a relatively longer life span since it is a metal or magnet.

According to the preferred embodiment of the present invention, the first retaining member 31 and the second retaining member 32 are both made of magnetic material. For instance, the first retaining member 31 is a metal having magnetic attracting ability, while the second retaining member 32 is a magnet; or the first retaining member 31 is a magnet, while the second retaining member 32 is metal having magnetic attracting ability; or the first retaining member 31 and the second retaining member 32 are both magnets, wherein the poles of the first retaining member 31 and the second retaining member 32 are opposite to each other so that the first retaining member 31 is capable of magnetically coupling with the second retaining member 32. In other words, when the glove 10 is at the storing position, the first retaining member 31 is coupled with the second retaining member 32 by magnetic attracting force in such a manner that the glove body 11 is retained on the retention spot so that the glove 10 is retained on the auxiliary element 20.

The auxiliary element 20 is an aiding tool for fixing the glove 10, as a typical example, the auxiliary element 20 is a retention board. In other words, the auxiliary element 20 is a tool for aiding the user to wear the glove 10 in a donning and doffing manner. The auxiliary element 20 provides a retention spot 21 which can be embodied as a retention surface, wherein the retention surface is provided with the second retaining member 32, so that the first retaining member 31 is coupled with the second retaining member 32 in such a manner that the glove 10 is retained on the retention surface.

Referring to FIG. 2 of the drawing, according to the preferred embodiment, the auxiliary element 20 comprises a retention board 22, wherein at least one glove 10 is detachably provided on the retention board 22, for example, the retention board 22 is provided with two retention spot 21, wherein a pair of gloves 10 with two glove bodies 11 are provided on the retention board 22. The auxiliary element 20 further comprises a supporting base 23, wherein the retention board 22 is extended from the supporting base 23 in such a manner that the retention board 22 is standing an upright position. It is worth to mention that the retention board 22 is at a position that the height thereof provides convenience for the user so that the user does not have to bend his body to wear the glove 10, instead he can simply stand in front of the retention board and simply by putting into or retracting his hands from the receiving cavity 12 of the glove 10 so that he can easily wear the glove 10 in a donning and doffing manner.

The first retaining member 31 is provided on the glove body 11 of the glove 10, according to the preferred embodiment, the first retaining member 31 is provided on the outer surface 14 of the glove body 11. Accordingly, the outer surface 14 of the glove body 11 has a palm side 141 and a dorsal side 142, wherein two end portions of the palm side 141 and the dorsal side 142 are sealedly closed while the two other end portions thereof are open so as to define the receiving cavity 12 and the opening 13. The first retaining member 31 can be provided on the palm side 141, the dorsal side or both. Since when the user uses the gloves 10, generally the palm side 141 has contact with chemical substance, food material or experiment instrument, so that the first retaining member 31 is preferably provided on the dorsal side 142 so as to prevent the first retaining member 31 from being damaged while in use.

According to the different configuration of the finger portion, the glove 10 can be a five-finger-portion glove, i. e. the five fingers of a hand is received in five finger portions of the glove 10 respectively; or a three-finger-portion glove, i. e. the thumb and the index finger are received in two finger portions respectively while the rest three fingers are received in one finger portion of the glove 10; or a two-finger-portion glove, i. e. the thumb is received in one of the finger portion of the glove 10 while the rest four fingers are received in the other finger portion of the glove 10; or an one-finger-portion glove, i. e. the five fingers are all received in a single finger portion of the glove 10. Accordingly, the more finger portions, the better warm keeping effect of the glove 10, but at the same time the movement of the fingers of the user is limited, while the five-finger-portion glove is convenient for the movement of the fingers of the user, so the configuration of the glove is varied according to different requirements of the user.

Accordingly, the glove body 11 comprises a closing portion 111 and an opening portion 112, wherein the opening 13 is provided at the opening portion 112. The closing portion 111 is adapted for receiving a hand of the user. According to this preferred embodiment, the closing portion 111 comprises a palm portion 1111, five finger portions 1112 so as to form a five-finger-portion glove 10.

The first retaining member 31 can be provided on the closing portion 111 of the glove body 11 or the opening portion 112 of the glove body 11. According to this preferred embodiment, the first retaining member 31 is provided on the opening portion 112 of the glove body 11 which is aligned with a root portion of the hand of the user. This design further facilitate the wearing of the glove 10, as the opening portion 112 of the glove body 11 is retained on the retention spot 21 of the auxiliary element 20, the user is convenient to put/retract out his hands into/from the receiving cavity 12 of the glove 10.

According to this preferred embodiment, the first retaining member 31 can be provided at the outer surface 14 of the glove 10, for example, the first retaining member 31 is protrudedly extended from the outer surface 14 of the glove 10, or the glove body 11 has a receiving hole at the outer surface and the first retaining member is embedded into the receiving hole in such a manner that an exposing surface of the retaining element 31 is engaged with the outer surface 14 of the glove 10 to form an integral surface. Correspondingly, the second retaining member also can be protrudedly extended from the auxiliary element 20 or embedded into the outer surface of the auxiliary element 20 at the retention spot 21 thereof.

FIG. 3A to FIG. 3E are schematic views illustrating the using of the glove arrangement of the present invention, wherein the glove 10 is adapted to move between an in-use position and a storing position with a help of the auxiliary element 20.

Referring to FIG. 3A to FIG. 3C of the drawings, the method for wearing the glove 10 of the glove arrangement in a donning manner is illustrated. As shown in FIG. 3A, when the glove 10 is at the storing position, the first retaining member 31 is coupled with the second retaining member 32, according to this preferred embodiment, the first retaining element 31 is magnetically coupled with the second retaining member 32 so that the glove 10 is retained on the retention board 22. When a user wants to wear on the glove body 11, referring to FIG. 3B of the drawing, he only need to put his hand into the receiving cavity 12 through the opening 13 of the glove 10, and the palm and fingers of the hand of the user are then received in the closing porting 111 of the glove body 11, since the existence of the magnetic attracting force between the first retaining member 31 and the second retaining member 32, the glove body 11 will not slip off from the retention board 22 when the user is donning the glove 10. Referring to FIG. 3C of the drawing, after wearing on the glove 10 which is retained on the retention board 22, applying an pulling force which is stronger than the magnetic attracting force between the first retaining member 31 and the second retaining member 32, i. e. the pulling force overcomes the magnetic attracting force, the user can take away the glove 10 so that the glove 10 escapes from the auxiliary element 20 and is ready for use by the user.

Figure 3E:
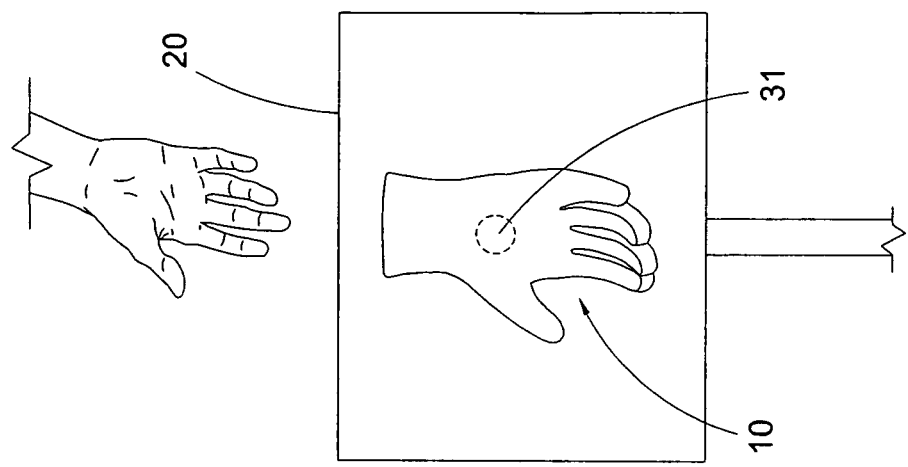
Figure 3D:
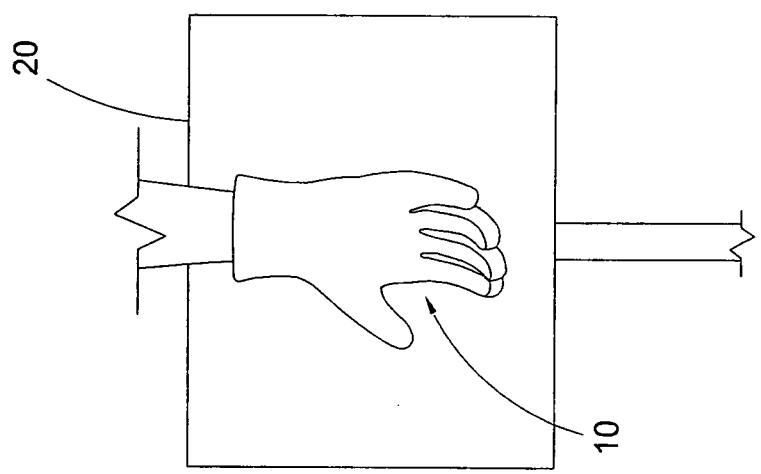

Referring to FIG. 3D and FIG. 3E of the drawings, placing the glove 10 towards the auxiliary element 20 in such a manner that the first retaining member 31 aligns with the second retaining member 32, and then the first retaining member 31 will automatically be attracted to the second retaining member 32 so that the glove 10 is retained on the auxiliary element 20. It is worth mentioning that when the first retaining member 31 and the second retaining members are corresponding Velcro members or bonding members, the user press the glove body 11 in such a manner that the first retained element 31 is fixed on the second retaining member 32 so that the glove body 11 of the glove 10 is retained on the retention spot 21 of the auxiliary element 20. And finally, as shown in FIG. 3E, the user retracts his hand out of the glove body 11 so as to doff the glove 10.

It is thus can be seen that the user only uses one hand to wear the glove 10 in a donning and doffing manner. And thus the hands of the user will not have skin contact with the outer surface 14 of the glove body 11. Furthermore, the glove 10 is retained on the auxiliary element 20 ready for use so that we don't have to waste time fumbling the gloves in a storing cabinet.

It is worth mentioning that the auxiliary element 20 comprises two retention spots 21, wherein a pair of glove 10 having two glove bodies 11 are detachably provided on the auxiliary element 20, in this preferred embodiment, two glove bodies 11 are detachably coupled with the retention board 22, so that the two hands of the user can simultaneously wear the two glove bodies 11 respectively in a donning and doffing manner.

In addition, when the glove 10 is at the storing position, the closing portion 111 of the glove body 11 is placed in a downward orientation while the opening portion 112 is orientated upwardly, in other words, the glove 10 is in a hand-down position in such a manner that the user simply and naturally put his hand downwardly into the receiving cavity 12 of the glove body 11 to wear the glove body 11 in a donning manner while retract up his hand from the receiving cavity 12 of the glove body 11 to wear the glove body in a doffing manner. It is worth mentioning that when the users wears the glove body 11 to have contact with chemical substance, the chemical substance will remain on the glove body 11, as the glove body 11 is retained on the auxiliary element in a hand down position, the chemical substance will naturally drop down towards the closing portion 111 so as to prevent the user from contacting with the outer surface 14 of the glove body 11 during donning and doffing operation.

Figure 4:
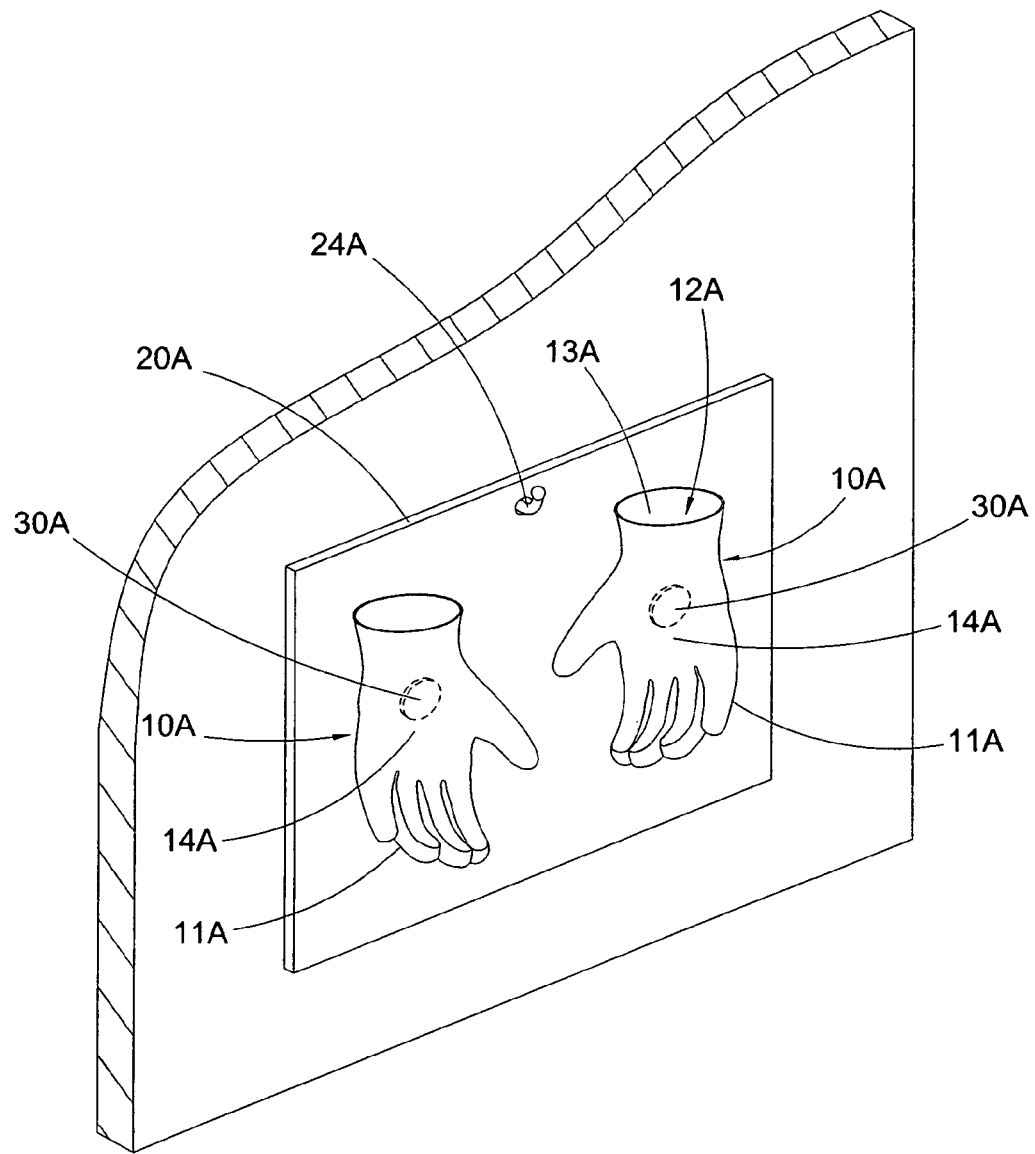
FIG. 4 is a perspective view of a glove arrangement according to a second preferred embodiment of the present invention.
Figure 5:
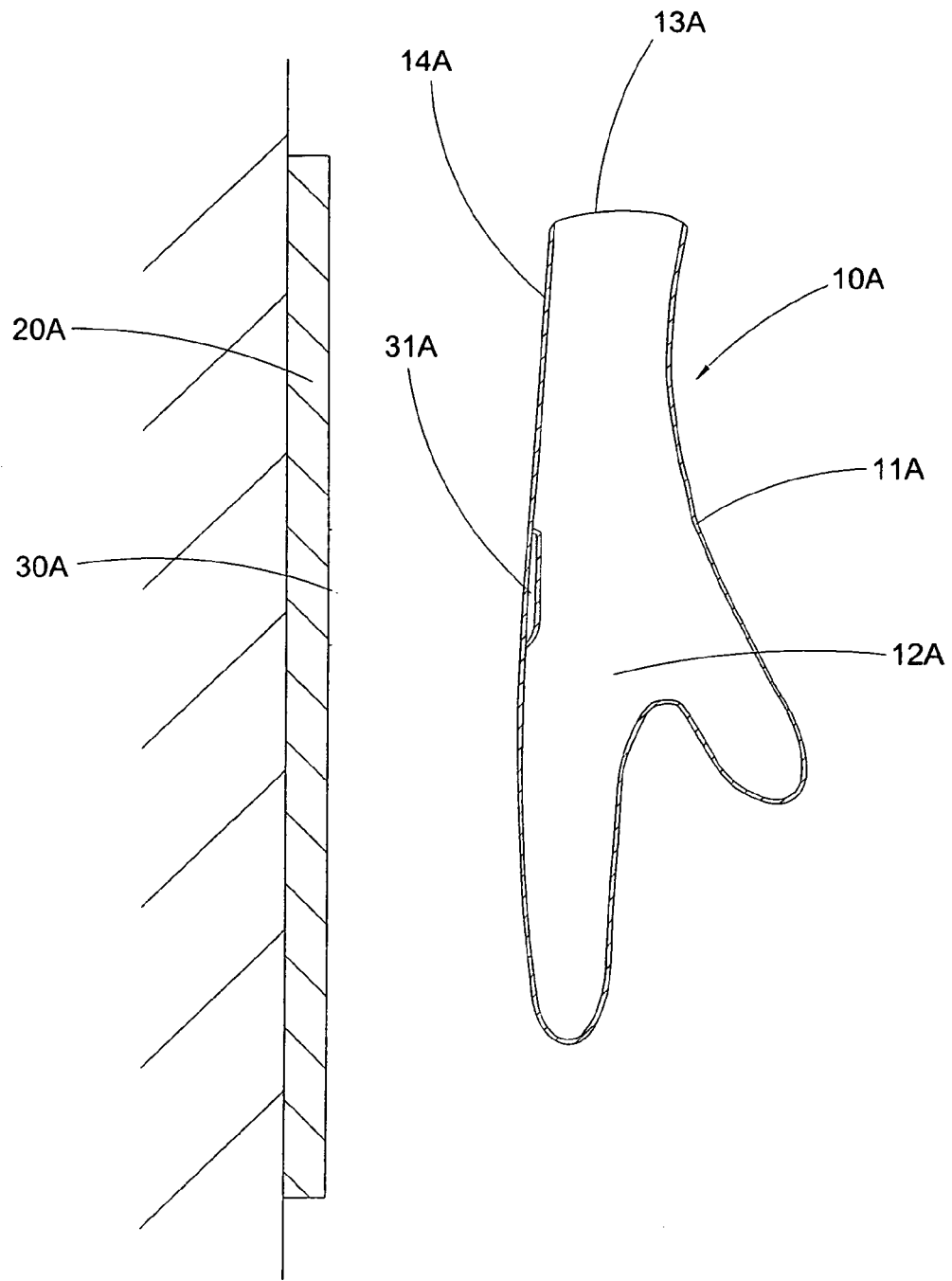
FIG. 5 is a sectional view of the glove arrangement according to the above preferred embodiment of the present invention.
Figure 6:
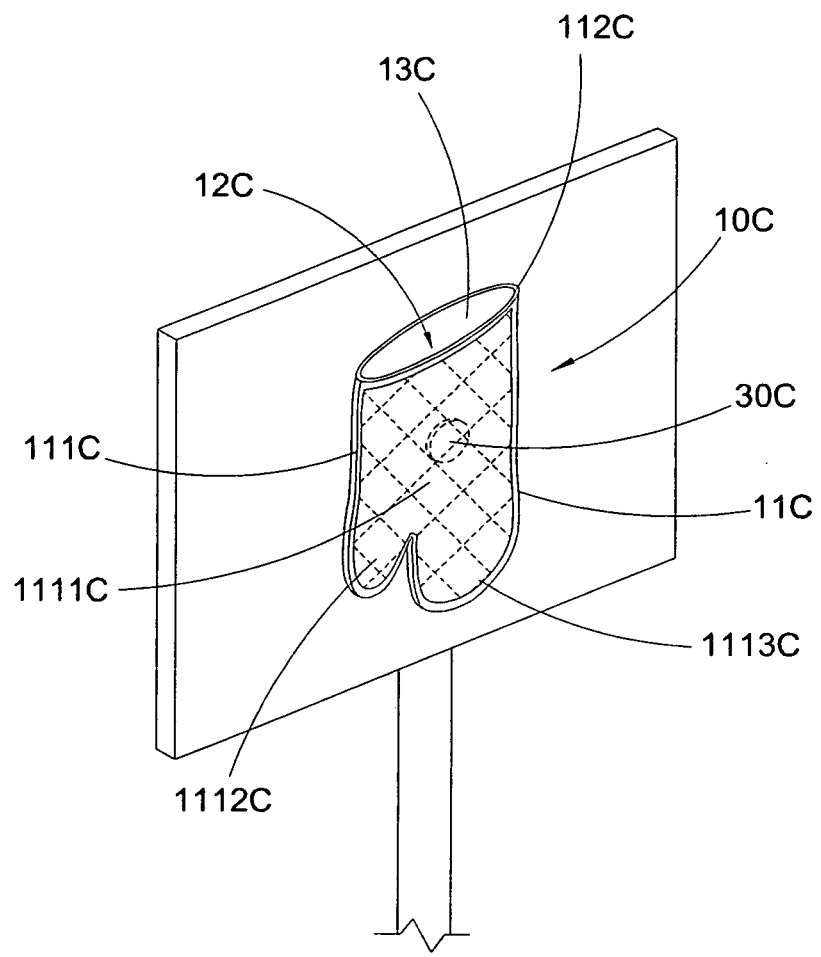
FIG. 6 is a perspective view of a glove arrangement according to a third preferred embodiment of the present invention.

Referring to FIG. 4 and FIG. 5 of the drawings, according to a second preferred embodiment of the present invention, wherein the glove arrangement comprises at least a glove 10A, an auxiliary element 20A and a retaining arrangement 30A. The glove 10A comprises a glove body 11A, wherein the glove body 11A defining a receiving cavity 12A and an opening 13A communicating with the receiving cavity 12A in such a manner that the receiving cavity 12A is communicated outside of the glove body 11A, and thus a user can put his hand into the receiving cavity 12A through the opening 13A. Therefore, the hand of the user is secured in the receiving cavity 12A so that the glove 10A can protect the hand or keep warm of the hand.

The auxiliary element 20A is a magnetic board having magnetic attracting ability such as a metal board or a magnet board, wherein the second retaining member 32A is embodied as the magnetic board, in other words, the second retaining member 32 is eliminated and the integral magnetic board function as the second retaining member 32 to detachably couple with the first retaining member 31A. Referring to FIG. 5 of the drawing, the first retaining member 31A is provide on the inner surface of the glove body 11A instead of exposing on the outer surface 14 of the glove body 11 according to the above preferred embodiment. And thus the first retaining member 31A is hidden in the receiving cavity 12A of the glove body 11A. Furthermore, since the second retaining member 32A is embodied as the integral magnetic board, the first retaining member 31A can be retained at any position on the surface of the auxiliary element 20A, in other words, the glove body 11A can be retained at any position on the surface of the auxiliary element 20A. As a typical example, the auxiliary element 20A is a metal board, while the first retaining member 31A is a magnet so that the retaining element 31A can be magnetically attracted at any position on the surface of the metal board.

It is note worthy that the auxiliary element 20A may further has a retaining hole 24A for coupling with a hook so that the auxiliary element 20A can be fixed on any environment surface like wall surface, instrument surface, furniture surface and so on. And thus the user can choose a desired location for placing the glove 10 of the glove arrangement.

Accordingly, the auxiliary element 20A may be eliminated, and the glove body 11A is directly detachably coupled on a magnetic environment surface, magnetic object surface or any magnetic instrument surface, and thus the globe body 11A can be retained thereon ready for using. And thus it further provides a convenience for the storing of the glove 10 and facilitates the access of the glove 10.

Referring to FIG. 6 to FIG. 9 of the drawings, a glove arrangement according to a third preferred embodiment of the present invention is illustrated, wherein the glove arrangement comprises at least a glove 10C and a retaining arrangement 30C, wherein the glove 10C is capable of being detachably mounted on a environment surface such as the surface of the microwave oven, toaster and refrigerator via the retaining arrangement 30C. Accordingly the auxiliary element 20 is eliminated in this preferred embodiment.

The glove 10C comprises a glove body 11C, wherein the glove body 11C defining a receiving cavity 12C and an opening 13C communicating with the receiving cavity 12C in such a manner that the receiving cavity 12C is communicated outside of the glove body 11C, and thus a user can put his hand into the receiving cavity 12C through the opening 13C. Therefore, the hand of the user is secured in the receiving cavity 12C so that the glove 10C can protect the hand or keep warm of the hand.

According to this preferred embodiment, the glove body 11C comprises a closing portion 111C and an opening portion 112C, wherein the opening 13C is provided at the opening portion 112C. The closing portion 111C is adapted for receiving a hand of the user. Accordingly, the closing portion 111C comprises a palm portion 1111C, a thumb portions 1112C and a third portion 1113C for receiving the rest four fingers so as to form a two-finger-portion glove 10C.

The retaining arrangement 30C comprises a first retaining member 31C and a second retaining member 32C, wherein the first retaining member 32C is provided on the glove body 11C, and the second retaining member 32C is capable of being detachably mounted to an environment surface. Accordingly, the first retaining member 31C comprises at least a magnetic element 311C, wherein the magnetic element 311C magnetically couple with the second retaining member 32C so that the glove body 11C is capable of detachably retained on the environment surface.

Figure 7:
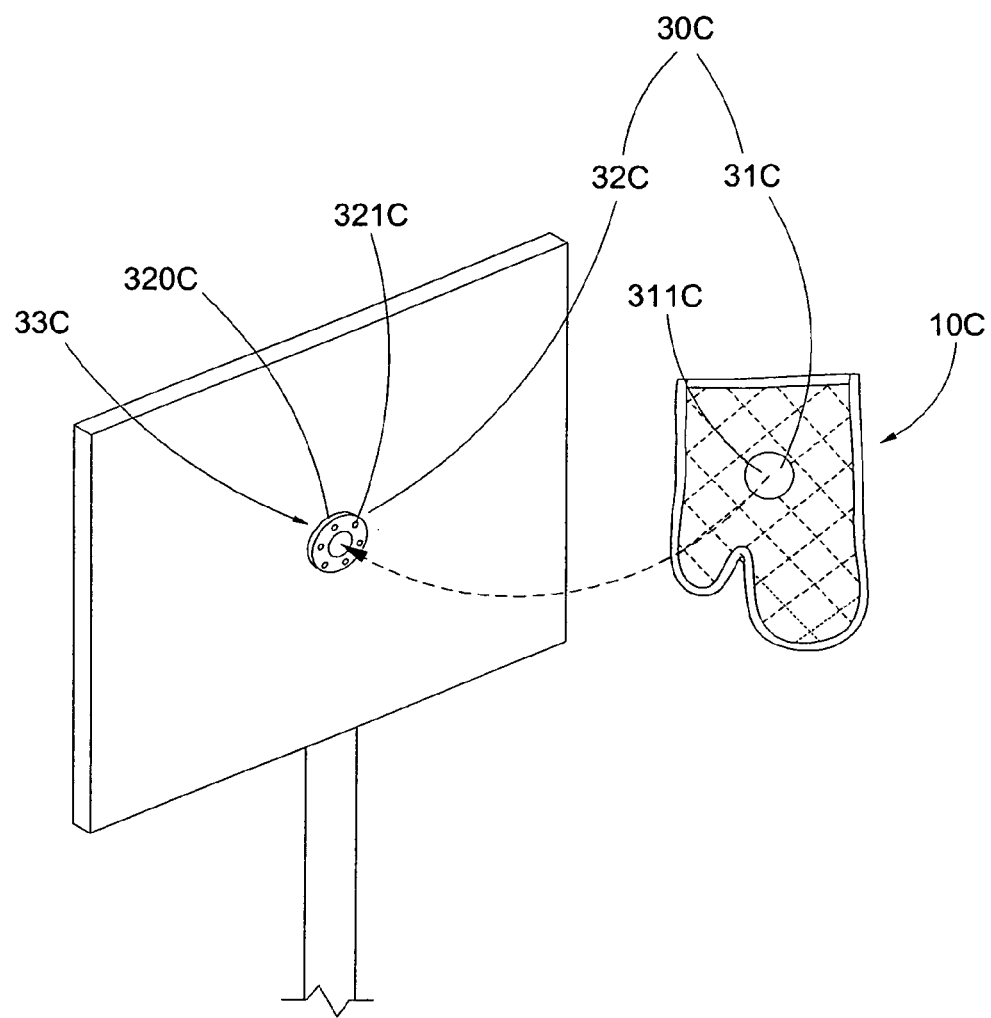
FIG. 7 is an exploded view of the glove arrangement according to the above third preferred embodiment of the present invention.

Referring to FIG. 7 of the drawing, the retaining arrangement 30C further comprises a fastening member 33C provided on the second retaining member 32C, wherein the fastening member 33C can be Velcro members, bonding members or a mounting tape, so that when the environment surface is not provided with magnet or metal, the second retaining member 32C can still be bonded to the non-magnetic surface. It is worth mentioning that the second retaining member 33C may be sewed to the environment surface. In other words, in this preferred embodiment, the second retaining member 32C is capable of being detachably mounted to an environment surface instead of being firmly fixed on the auxiliary element or the environment surface in the above preferred embodiments. Accordingly, the second retaining member 32C is being detachably mounted to the magnetic surface via magnetic attracting force or being detachably mounted to non-magnetic surface via the fastening member 33C. In other words, according to this preferred embodiment, unlike the above preferred embodiments in which the second retaining member 32 is previously fixed on the retention spot 21 of the auxiliary element 20, the second retaining member 32C is detachably mounted to an environment surface, so that it provides more convenience for selecting the storing position of the glove 10C.

Accordingly, the glove body 11C is detachably mounted to an environment surface via the second retaining member 32C so that the outer surface of the glove body 11C does not have contact with the environment surface. In other words, the second retaining member 32C not only mounts the glove body 11C to the environment surface but also keep a distance between the glove body 11C and the environment surface. And thus when the glove 10 is used in chemical industry or biological experiments, the outer surface of the glove body 11C will be contaminated by chemical substance, but since the glove body 11C is coupled with the second retaining member 32C via the first retaining member 31C, the outer surface of the glove body 11C will not have contact with the environment surface. And thus the chemical residue on the outer surface of the glove body 11C will not result in a pollution to the environment surface.

Preferably, the magnetic element 311C of the first retaining member 31C is a magnetic sheet laminated on the outer surface of the glove body 11C. The second retaining member 32C comprises a housing 320, at least a corresponding coupling element 321C and a fixing element 322C. Accordingly, the coupling element 321C also can be a magnetic sheet having a different pole with the magnetic element 311C of the first retaining member 31C so that the first retaining member 31C is detachably coupled with the second retaining member 32C and defining a first magnetic attracting force.

It is worth mentioning that the magnetic sheet is made of magnetic material and bonding material, the magnetic material can be ferrites, Nd—Fe—B permanent magnets, samarium-cobalt magnets and the like. The bonding material can be any additives like Buna-N rubber, ethylene resin, epoxy resin, phenol formaldehyde resin and the like.

Figure 8:
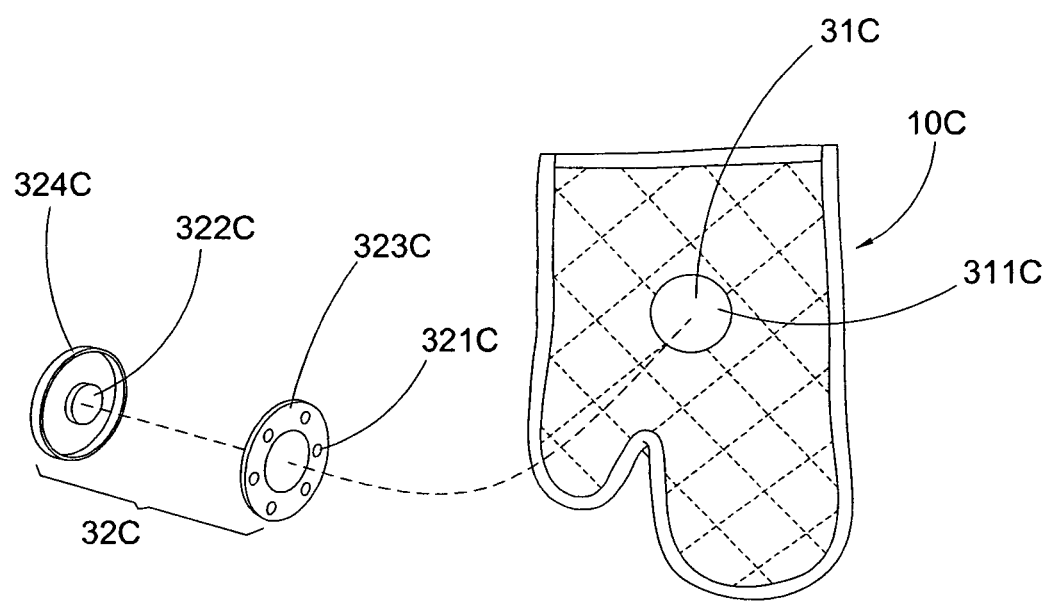
FIG. 8 is an exploded view of a retaining arrangement of the glove arrangement according to the above third preferred embodiment of the present invention.

The fixing member 322C of the second retaining member 32C is an magnet, as shown in FIG. 8, so that the second retaining member 32C is capable of magnetically coupling with an magnetic environment surface such as the outer surface of the refrigerator, microwave oven and toaster, wherein a second magnetic attracting force is defined between the second retaining member 32C and the magnetic environment surface.

It is worth mentioning that the first magnetic attracting force is smaller than the second magnetic attracting force. In other words, the first magnetic attracting force between the magnetic element 311 of the glove body 11 and the coupling element 321 of the second retaining member 32C is a relatively weaker force in comparison with the second magnetic attracting force. And thus when the glove 10C is retained on an environment surface via the retaining arrangement 30C, the user puts his hand into the glove body 11C and applies an outward pulling force so that he can take way the glove body 11 from the environment surface, but since the second magnetic attracting force between the second retaining member 32C and the environment surface is relatively stronger, the second retaining member will still remains on the environment surface, as shown in FIG. 7.

More specifically, referring to FIG. 8 of the drawing, the housing 320C of the second retaining member 32C comprises a first casing 323C and a second casing 324C, in other words, the first casing 323C is matched with the second casing 324C to form the integral housing 320C. The first casing 323C is provided with at least a coupling element 321C for coupling with the magnetic sheet of the magnetic element 311C of the first retaining member 31C, and the second casing 324C is provided with the fixing element 322C which is embodied as a magnet, preferably, the fixing element 322C is embedded into the chamber of the second casing 324C so that it is not exposed outside so as to enhance an aesthetic appearance of the second retaining member 32C, as shown in FIG. 8. It is worth mentioning that the positions of the coupling element 321C and the fixing element 322C do not face to each other. For example, the first casing 323C is a round disk while the second casing 324C is a case having a chamber defining an opening, the first casing 323C is pressed into the chamber of the second casing 324C to seal said opening so as form a cylinder housing 320C, wherein the fixing element 322C is provided at the center of the chamber of the second casing 324C while the first casing 323C comprises six coupling elements 321C provided along the outer circumference thereof for magnetically coupling with the magnetic element 311C.

It is worth mentioning that both side surfaces, i. e. the palm side and the dorsal side, of the glove body 11C of the glove 10C are provided magnetic elements 311C so that both side of the glove body 11C can be detachably coupled with the second retaining member 32C.

Alternatively, the glove body 11C has a operation surface and a non-operation surface, and preferably the magnetic element 311C of the first retaining member 31C is provided on the non-operation surface.

Figure 9:
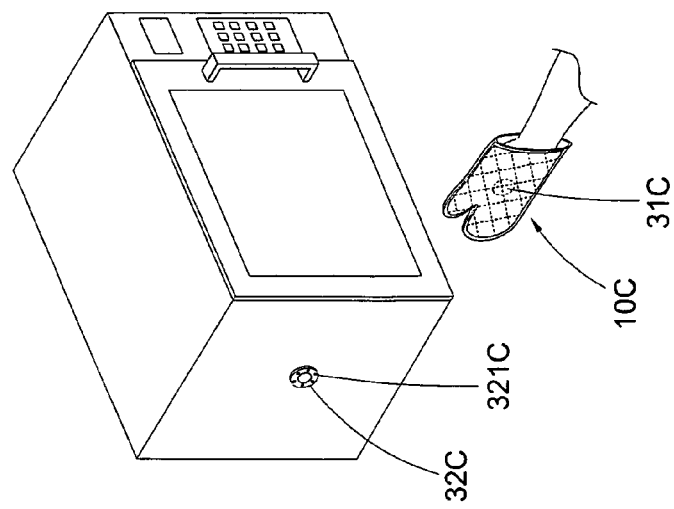
FIG. 9 is a schematic view illustrating the glove in a using position according to the above preferred embodiment of the present invention.
Figure 9:
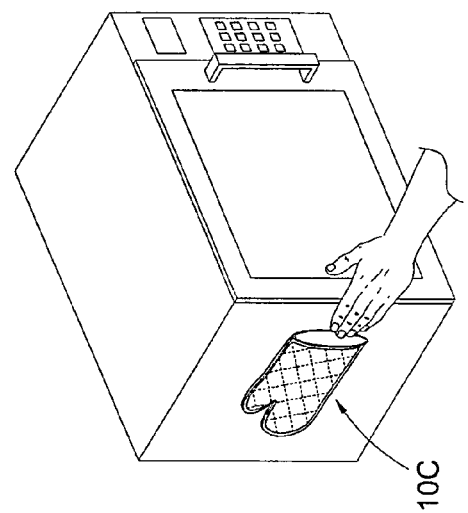
Figure 9:
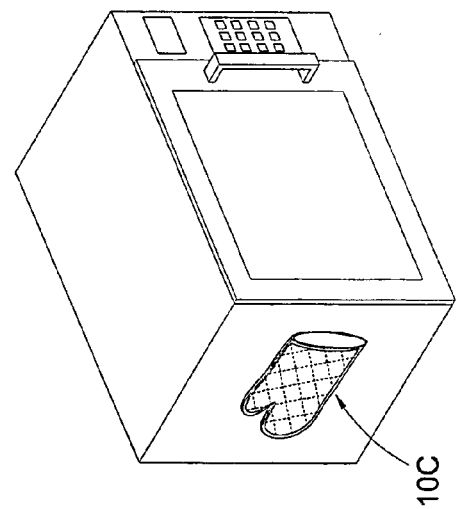

Referring to FIG. 9 of the drawing, the glove arrangement of the present invention is introduced into household application, for example, the user wears the glove 10C for preventing from burning when he uses the microwave oven or toaster. Accordingly, the second retaining member 32C is previously mounted on the environment surface, since the second retaining member 32C is provided with a fixing member 322 which is a magnet so that the second retaining member 32C is magnetically mounted to the magnetic environment surface. Alternatively, the second retaining member 32C is affixed to the environment surface by a mounting tape, bonding glue or the second retaining member 32 is sewed to the environment surface. And the affixing position of the second retaining member 32C is adjusted to a handy position so that the glove 10C is convenient for using. When the glove body 11C is parallelly aligned with the second retaining member 32C in such a manner that the magnetic element 311C aligns with the coupling element 321C, the gloved body 11C will be engaged with the second retaining member 32C so that the glove body 11C is retain on the environment surface.

When the user wants to use the glove 10C, simply slides his hand into the receiving cavity 12C of the glove body 11C so that he can wear the glove body 11C in a donning manner. It is note worthy that when the second retaining member is magnetically mounted to an magnetic environment surface and defines a second magnetic attracting force therebetween, the first magnetic attracting force between the second retaining member 32C and the first retaining member 31C is relatively smaller than the second magnetic attracting force. And thus the user can apply a relatively weaker pulling force and takes away the glove body 11C from the second retaining member 32C, while the second retaining member 32C is still remained on the magnetic environment surface. And finally, when the user finishes the operation, it's also convenient for him to return the glove body 11C to the original spot.

It is thus can be seen that since the glove body 11C of this preferred embodiment is capable of being detachably mounted to an environment surface via the retaining arrangement 30C by magnetically attracting means or other bonding means, so that the glove body 11C can be provided at any handy position convenient for the user to operate. Therefore the user no longer need to fumble the glove 10C when he wants to use the glove 10C immediately. Furthermore, the user only need one hand to wear the glove body 11 in a donning and doffing manner without the help of the other hand.

Figure 10:
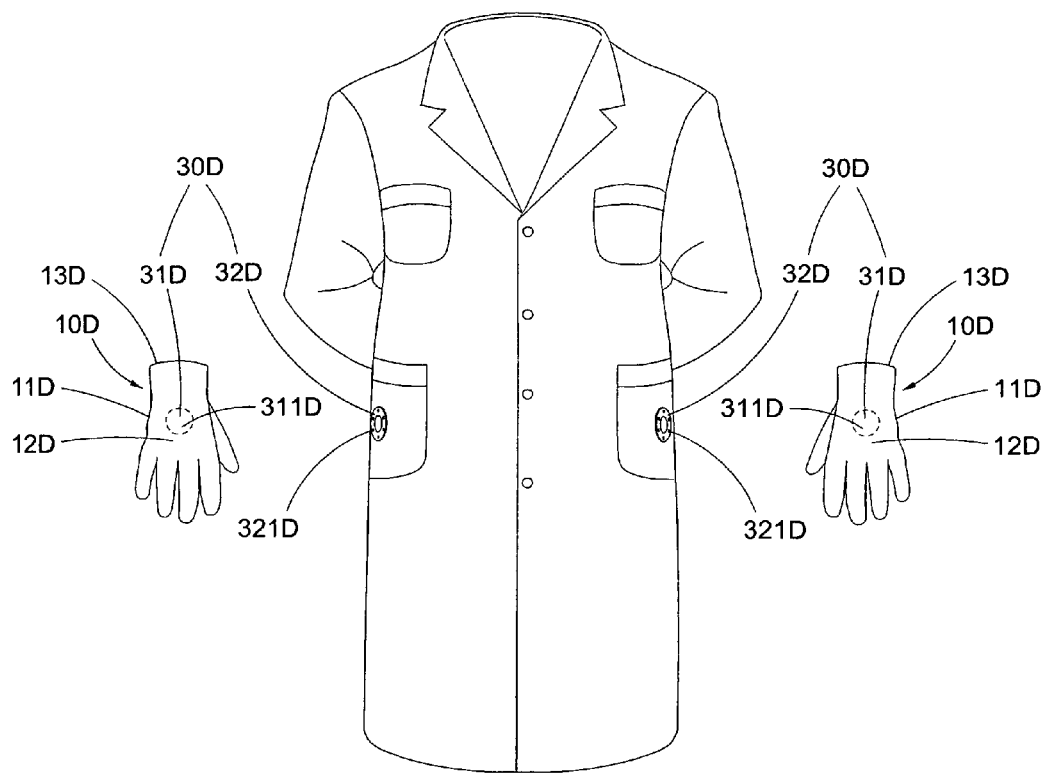
FIG. 10 is a perspective view of a glove arrangement according to a fourth preferred embodiment of the present invention.

Referring to FIG. 10 of the drawing, according to a fourth preferred embodiment of the present invention, a glove arrangement which is suitable for using in chemical industry and experiments in labs is illustrated, wherein the glove arrangement comprises at least a glove 10D and a retaining arrangement 30D.

The glove 10D comprises a glove body 11D, wherein the glove body 11D defining a receiving cavity 12D and an opening 13D communicating with the receiving cavity 12D in such a manner that the receiving cavity 12D is communicated outside of the glove body 11D, and thus a user can put his hand into the receiving cavity 12D through the opening 13D. Therefore, the hand of the user is secured in the receiving cavity 12D so that the glove 10D can protect the hand.

Accordingly, the glove 10D is detachably mounted to the user's clothes such as a working suit and a smock, in other words, in this preferred embodiment, the environment surface is the surface of the user's clothes. For example, two glove bodies 10D are provided at two sides of a smock. When the user wants to use the glove 10D, he just naturally put his hand into the receiving cavity 12D so that he can wear the glove body 11D, and when the operation is done, he can simply return the glove body 11D to the smock, it is very convenient for using.

Accordingly, the retaining arrangement 30D comprises a first retaining member 31D and a second retaining member 32D, wherein the first retaining member 31D is provides on the glove body 11D, and the second retaining member 32D is provided on the clothes of the user, wherein the first retaining member 31D is detachably coupled with the second retaining member 32D so that the glove 10D is detachably mounted on the clothes of the user.

The first retaining member 31D and the second retaining member 32D are corresponding magnetic members, Velcro members or bonding members, so that the first retaining member 31D is capable of detachably coupling with the second retaining member 32D, it is worth mentioning that the engaging force between the first retaining member 31D and the second retaining member 32D is strong enough so that the glove 10D will not slip off or fall off from the clothes of the user. Preferably the first retaining member 31D is magnetically coupled with the second retaining member 32D.

Alternatively, the first retaining member 31D comprise at least a magnetic element 311D which is a magnetic sheet, while the second retaining member 32D comprises a plurality of coupling element 321D which also can be embodies as magnetic sheets disclosed in the above third preferred embodiment. And thus the glove body 11D is detachably provided on the clothes of the user via the magnetic attracting force between the first retaining member 31D and the second retaining member 32D.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A glove arrangement comprising at least a glove and a retaining arrangement, wherein said retaining arrangement detachably retain said glove on an environment surface so that said glove is adapted to move between an in-use position and a storing position, wherein when said glove is at said in-use position, said glove is departed from said environment surface for operation by a user, wherein at said storing position, said glove is retained on said environment surface, wherein said retaining arrangement comprises a first retaining member provided on said glove and a second retaining member being detachably mounted on said environment surface, wherein said first retaining member is detachably coupled with said second retaining member in such a manner that said glove is capable of being detachably mounted to said environment surface, wherein said first retaining member comprises a magnetic element, wherein said second retaining member comprises at least a coupling element and a fixing element, wherein said coupling element is magnetically coupled with the magnetic element, and said fixing element is detachably mounted to said environment surface, wherein said magnetic element of said first retaining member is a magnetic sheet laminated on said glove, wherein said coupling element of said second retaining member is a corresponding magnetic sheet having an opposite pole with said magnetic element of said first retaining member, such that first retaining member is magnetically coupled with said second retaining member and define a first magnetic attracting force therebetween; wherein said fixing member is a magnet for magnetically mounting to the environment surface and defines a second magnetic attracting force therebetween, wherein said first magnetic attracting force is relatively smaller than said second magnetic attracting force.

2. The glove arrangement, as recited in claim 1, wherein said second retaining member further comprises a housing having a first casing and a second casing, wherein said magnetic element of said first retaining member is provided on said first casing and said fixing element of said second retaining member is provided on said second casing.

3. The glove arrangement, as recited in claim 2, wherein said first casing is a round disk and said second casing is a case defining a chamber having an opening, wherein said first casing is pressed into said chamber of said second casing to seal said opening so as to form said housing in a cylinder shape, wherein said fixing element is provided at a center of said chamber of said second casing and said first casing comprises six said coupling elements provided along said outer circumference thereof for magnetically coupling with said magnetic element.

4. The glove arrangement, as recited in claim 3, wherein said glove comprises a glove body having an operation surface and a non-operation surface, wherein said magnetic element of said first retaining member is provided on said non-operation surface.

5. The glove arrangement, as recited in claim 3, wherein said glove comprises a glove body having a palm side and a dorsal side, wherein two said magnetic elements of said first retaining member is provided on said palm side and said dorsal side respectively, so that both said palm side and said dorsal side of said glove body are capable of being detachably mounted to said environment surface via said second retaining member.

* * * * *